US012643918B2

(12) United States Patent
Edlund et al.

(10) Patent No.: US 12,643,918 B2

(45) Date of Patent: Jun. 2, 2026

(54) THIADIAZOLONE DERIVATIVES AND THEIR USE AS AMPK AGONISTS FOR THE TREATMENT OF DIABETES AND RELATED DISORDERS

(71) Applicant: Betagenon AB, Umeå (SE)

(72) Inventors: Thomas Edlund, Umeå (SE); Jacob Westman, Järlåsa (SE)

(73) Assignee: Betagenon AB, Umeå (SE)

( * ) Notice: Subject to any disclaimer, the term of this patent is extended or adjusted under 35 U.S.C. 154(b) by 606 days.

(21) Appl. No.: 18/028,192

(22) PCT Filed: Sep. 30, 2021

(86) PCT No.: PCT/GB2021/052535

§ 371 (c)(1),
(2) Date: Mar. 23, 2023

(87) PCT Pub. No.: WO2022/069894

PCT Pub. Date: Apr. 7, 2022

(65) Prior Publication Data

US 2023/0382930 A1 Nov. 30, 2023

(30) Foreign Application Priority Data

Oct. 1, 2020 (GB) ..................................... 2015585

(51) Int. Cl.
*C07F 9/6539* (2006.01)
*C07D 285/08* (2006.01)

(52) U.S. Cl.
CPC ........ *C07F 9/65397* (2013.01); *C07D 285/08* (2013.01)

(58) Field of Classification Search
CPC ......................... C07F 9/65397; C07D 285/08
See application file for complete search history.

(56) References Cited

U.S. PATENT DOCUMENTS 9,162,994 B2 10/2015 Westman et al.
9,675,596 B2 6/2017 Westman et al.
(Continued)

FOREIGN PATENT DOCUMENTS

WO WO-2011004162 A2 * 1/2011 ................ A61P 3/10
WO WO-2013108026 A1 * 7/2013 ........... C07D 285/08
(Continued)

OTHER PUBLICATIONS

Kim J, Yang G, Kim Y, Kim J, Ha J. AMPK activators: mechanisms of action and physiological activities. Exp Mol Med. Apr. 1, 2016; 48(4). (Year: 2016).*
(Continued)

*Primary Examiner* — George W Kosturko
*Assistant Examiner* — Izabela Schmidt
(74) *Attorney, Agent, or Firm* — MORRISON & FOERSTER LLP

(57) ABSTRACT

The invention relates to a compound of formula I, wherein: $R^1$ is as defined in the specification, or a pharmaceutically acceptable salt or solvate thereof, which compounds are useful in the treatment of a disorder or condition ameliorated by the activation of AMPK, particularly as prodrugs.

I (Continued)

17 Claims, 2 Drawing Sheets

(56) References Cited

U.S. PATENT DOCUMENTS

| | | | |
|---|---|---|---|
| 11,691,954 | B2 | 7/2023 | Edlund et al. |
| 12,162,850 | B2 | 12/2024 | Edlund et al. |
| 2022/0023269 | A1 | 1/2022 | Edlund et al. |
| 2023/0096218 | A1 | 3/2023 | Edlund et al. |
| 2024/0082222 | A1 | 3/2024 | Edlund et al. |
| 2024/0140921 | A1 | 5/2024 | Edlund et al. |
| 2025/0136563 | A1 | 5/2025 | Edlund et al. |
| 2025/0289791 | A1 | 9/2025 | Edlund et al. |

FOREIGN PATENT DOCUMENTS

| | | | | |
|---|---|---|---|---|
| WO | WO-2020095010 | A1 * | 5/2020 | ................ A61P 3/10 |
| WO | WO-2022069894 | A1 | 4/2022 | |
| WO | WO-2025017193 | A1 | 1/2025 | |
| WO | WO-2025017194 | A1 | 1/2025 | |
| WO | WO-2025027205 | A1 | 2/2025 | |
| WO | WO-2025252672 | A1 | 12/2025 | |

OTHER PUBLICATIONS

Berge et al., (1977). "Pharmaceutical salts," J. Pharmaceutical Sciences, 66:1-19.

Das et al., (2019). "AMP-activated protein kinase (AMPK) activator drugs reduce mechanical allodynia in a mouse model of low back pain," Reg Anesth Pain Med, 44:1010-1014.

Das et al., (2019). "Antihyperalgesia effect of AMP-activated protein kinase (AMPK) activators in a mouse model of postoperative pain," Reg Anesth Pain Med, 44:781-786.

Hawley et al., (2016). "The Na+/Glucose Cotransporter Inhibitor Canagliflozin Activates AMPK by Inhibiting Mitochondrial Function and Increasing Cellular AMP Levels," Diabetes, 65(9):2784-2794.

International Search Report and Written Opinion received for International Patent Application No. PCT/GB2021/052535 mailed on Jan. 24, 2022, 8 pages.

International Search Report and Written Opinion received for International Patent Application No. PCT/GB2022/052234 mailed on Jan. 23, 2023, 13 pages.

Steneberg et al., (2018). "PAN-AMPK activator 0304 improves glucose homeostasis and microvascular perfusion in mice and type 2 diabetes patients," JCI Insight, 3(12):e99114, 19 pages.

Villani et al., (2016). "The diabetes medication Canagliflozin reduces cancer cell proliferation by inhibiting mitochondrial complex-I supported respiration," Molecular Metabolism, 5(10):1048-1056.

Zhao et al., (2020). "From overnutrition to liver injury: AMP-activated protein kinase in nonalcoholic fatty liver diseases," J. Biol. Chem., 295(34):12279-12289.

Castro et al., (2008). "Non-ATP competitive glycogen synthase kinase 3beta (GSK-3beta) inhibitors: Study of structural requirements for thiadiazolidinone derivatives," Bioorganic & Medicinal Chemistry, 16:495-510.

* cited by examiner

THIADIAZOLONE DERIVATIVES AND THEIR USE AS AMPK AGONISTS FOR THE TREATMENT OF DIABETES AND RELATED DISORDERS

CROSS REFERENCE TO RELATED APPLICATIONS

This application is a national stage application under 35 U.S.C. § 371 of International Application No. PCT/GB2021/052535, filed internationally on Sep. 30, 2021, which claims the benefit of Great Britain Application No. 2015585.9, filed on Oct. 1, 2020.

FIELD OF THE INVENTION

The present invention relates to novel compounds, and the use of such compounds in medicine. In particular, the present invention relates to compounds that are useful in treating a disorder or condition ameliorated by the activation of AMP-activated protein kinase.

BACKGROUND OF THE INVENTION

AMP-activated protein kinase (AMPK) is a protein kinase enzyme that consists of three protein sub-units and is activated by hormones, cytokines, exercise, and stresses that diminish cellular energy state (e.g. glucose deprivation). Activation of AMPK increases processes that generate adenosine 5'-triphosphate (ATP) (e.g., fatty-acid oxidation) and restrains others such as fatty acid-, glycerolipid- and protein-synthesis that consume ATP, but are not acutely necessary for survival. Conversely, when cells are presented with a sustained excess of glucose, AMPK activity diminishes and fatty acid-, glycerolipid- and protein-synthesis are enhanced. AMPK thus is a protein kinase enzyme that plays an important role in cellular energy homeostasis. Therefore, the activation of AMPK is coupled to glucose lowering effects and triggers several other biological effects, including the inhibition of cholesterol synthesis, lipogenesis, triglyceride synthesis, and the reduction of hyperinsulinemia.

Given the above, AMPK is a preferred target for the treatment of the metabolic syndrome and especially type 2 diabetes. AMPK is also involved in a number of pathways that are important for many different diseases (e.g. AMPK is also involved in a number of pathways that are important in CNS disorders, fibrosis, osteoporosis, heart failure and sexual dysfunction).

AMPK is also involved in a number of pathways that are important in cancer. Several tumour suppressors are part of the AMPK pathway. AMPK acts as a negative regulator of the mammalian TOR (mTOR) and EF2 pathway, which are key regulators of cell growth and proliferation. The deregulation may therefore be linked to diseases such as cancer (as well as diabetes). AMPK activators may therefore be of utility as anti-cancer drugs.

It has been shown that AMPK activator drugs (e.g. metformin and 4-chloro-N-[2-[(4-chlorophenyl)methyl]-3-oxo-1,2,4-thiadiazol-5-yl]benzamide (i.e. the compound of formula II below)) are effective at treating pain. Das and co-workers report that, following lumbar disc puncture, postinjury treatment in mice with AMPK activator drugs reduces mechanical hypersensitivity (Das V, et al. Reg Anesth Pain Med 2019; 0:1-5. doi:10.1136/rapm-2019-100839). Similarly, Das and co-workers also report that early treatment with AMPK activator drugs reduces mechanical hypersensitivity in a postoperative pain model in mice (Das V, et al. Reg Anesth Pain Med 2019; 0:1-6. doi:10.1136/rapm-2019-100651). These drugs also normalize the AMPK pathway in the dorsal root ganglion. AMPK activators may therefore be used in the treatment of pain, particularly post-operative pain.

It has also been shown that hepatic steatosis may be regulated by AMPK (Zhao et al. J. Biol. Chem. 2020 295: 12279-12289). Activation of AMPK inhibits de novo lipogenesis while promoting fatty acid oxidation (β-oxidation) in the liver. AMPK activation also reduces free fatty acid release from adipose tissue and prevents hepatic steatosis. Pharmacological activation of AMPK in the liver was reported to promote beneficial effects on multiple aspects of non-alcoholic fatty liver disease (NAFLD). For example, activation of AMPK was found to improve non-alcoholic steatohepatitis (NASH) in both murine and simian animal models. Accordingly, AMPK activators may be useful in the treatment of NAFLD and NASH.

An example of an AMPK activator is 4-chloro-N-[2-[(4-chlorophenyl)methyl]-3-oxo-1,2,4-thiadiazol-5-yl]benzamide (i.e. the compound of formula II), which was first disclosed in WO 2011/004162.

II

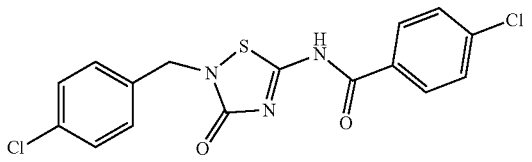

As an AMPK agonist (i.e. an AMPK activator), the compound of formula II is useful in the treatment of disorders or conditions which are ameliorated by the activation of AMPK. Such compounds may be useful in the treatment of cardiovascular disease (such as heart failure), diabetic kidney disease, type 2 diabetes, insulin resistance, non-alcoholic fatty liver disease, non-alcoholic steatohepatitis, pain, opioid addiction, obesity, cancer, inflammation (including chronic inflammatory diseases), autoimmune diseases, osteoporosis and intestinal diseases.

Although a number of AMPK activators are known, there is still a need for the development of novel compounds for the treatment of a disorder or condition ameliorated by the activation of AMPK. The inventors have now found novel compounds that are metabolised in vivo to form a known AMPK activator, with a surprising enhancement of the bioavailability of the AMPK activator. Said compounds were also found to activate AMPK.

The listing or discussion of an apparently prior-published document in this specification should not necessarily be taken as an acknowledgement that the document is part of the state of the art or is common general knowledge.

DETAILED DESCRIPTION OF THE INVENTION

In a first aspect of the invention, there is provided a compound of formula I

I

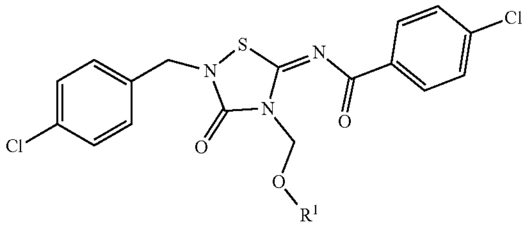

wherein $R^1$ is selected from the group consisting of —C(O)—$C_2H_4$—$CO_2H$ and —$PO_3H_2$, or a pharmaceutically acceptable salt or solvate thereof.

These compounds, including pharmaceutically acceptable salts and solvates thereof, may be referred to herein as the "compounds of the invention".

The compounds of the invention have been found to metabolise in vivo to form 4-chloro-N-[2-[(4-chlorophenyl)methyl]-3-oxo-1,2,4-thiadiazol-5-yl] benzamide (referred to herein as a compound of formula II) which is known to be an AMPK activator. In this regard, the compounds of the invention may be considered to be prodrugs of 4-chloro-N-[2-[(4-chlorophenyl)methyl]-3-oxo-1,2,4-thiadiazol-5-yl] benzamide.

Pharmaceutically acceptable salts include base salts. Such salts may be formed by conventional means, for example by reaction of a free acid or phosphate form of a compound of the invention with one or more equivalents of an appropriate base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Pharmaceutically acceptable salts of potential utility include those discussed in J. Pharmaceutical Sciences, 66: 1-19 (1977), by Berge et al. In some embodiments, the salts can be prepared in situ during the final isolation and/or purification for a compound of the invention, or separately by reaction of the free acid function with a suitable inorganic or organic base. Suitable counterions for said salts include, but are not limited to, metals, such as sodium, potassium and calcium, or amines, such as triethylammonium and lysine. Particular pharmaceutically acceptable addition salts that may be mentioned include alkali metal salts, alkaline earth metal salts or quaternary ammonium salts of the compound of formula I.

"Alkali metals" are metals found, along with hydrogen, in group I of the periodic table, most notably lithium, sodium, potassium, rubidium and caesium. It will therefore be understood that an "alkali metal salt" is a chemical compound consisting of an assembly of one or more alkali metal cations and one or more associated anions.

"Alkaline earth metals" are metals found in group II of the periodic table, most notably magnesium, calcium, strontium and barium. It will therefore be understood that an "alkaline earth metal salt" is a chemical compound consisting of an assembly of one or more alkaline earth metal cations and one or more associated anions.

"Quaternary ammonium" cations are positively charged ions of the structure $[NR_4]^+$, where each R may independently represent H, a $C_{1-6}$ alkyl group, a $C_{2-6}$ alkenyl group, a $C_{2-6}$ alkynyl group or an aryl group. Alternatively, a "quaternary ammonium" cation is a cationic form (particularly a protonated form) of an amino acid, such as an amino acid bearing a positively charged side chain (e.g. lysine, histidine or arginine). It will therefore be understood that a "quaternary ammonium salt" is a chemical compound consisting of an assembly of one or more quaternary ammonium cations and one or more associated anions.

Unless otherwise specified, alkyl groups defined herein may be straight-chain or, when there is a sufficient number (i.e. a minimum of two or three, as appropriate) of carbon atoms, be branched-chain, and/or cyclic (so forming a cycloalkyl group). When there is a sufficient number (i.e. a minimum of four) of carbon atoms, such groups may also be part cyclic (so forming a partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl.

Unless otherwise specified, alkenyl groups defined herein may be straight-chain or, when there is a sufficient number (i.e. a minimum of three) of carbon atoms, be branched-chain. For the avoidance of doubt, particular alkenyl groups that may be mentioned include straight chain (i.e. not branched) alkenyl groups.

Unless otherwise specified, alkynyl groups defined herein may be straight-chain or, when there is a sufficient number (i.e. a minimum of four) of carbon atoms, be branched-chain. For the avoidance of doubt, particular alkynyl groups that may be mentioned include straight chain (i.e. not branched) alkynyl groups.

For the avoidance of doubt, unless otherwise specified, groups referred to herein as "alkyl", "alkenyl" and/or "alkynyl" will be taken as referring to the highest degree of unsaturation in a bond present in such groups. For example, such a group having a carbon-carbon double bond, and, in the same group, a carbon-carbon triple bond will be referred to as "alkynyl".

As may be used herein, the term aryl may refer to aromatic groups. Such groups may be monocyclic or bicyclic and, when bicyclic, be either wholly or partly aromatic. aryl groups that may be mentioned include $C_{6-10}$ aryl groups, particularly phenyl, naphthyl, 1,2,3,4-tetrahydronaphthyl, indanyl, and the like (e.g. phenyl and naphthyl). For the avoidance of doubt, the point of attachment of substituents on aryl groups may be via any suitable carbon atom of the ring system.

Accordingly, an "alkali metal salt", "alkaline earth metal salt" or "quaternary ammonium salt" of a compound of formula I refers to a compound comprising one or more alkali metal, alkaline earth metal or quaternary ammonium cations (e.g. lithium, magnesium, calcium, ammonium, tetramethylammonium and, particularly, sodium and potassium) and one or more anions of a compound of formula I.

Particular, alkali metal, alkaline earth metal and quaternary ammonium salts of a compound of formula I that may be mentioned include compounds of formula III,

III

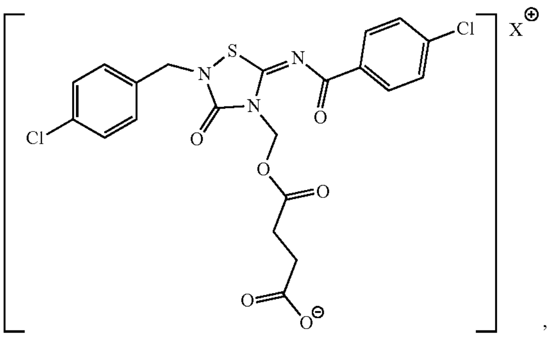

, and formula IV,

IV

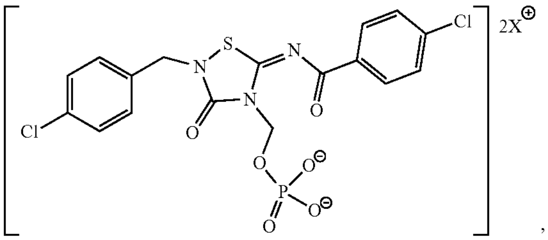

, wherein $X^+$ represents an alkali metal, alkaline earth metal or quaternary ammonium (e.g. lithium, magnesium, calcium, ammonium, tetramethylammonium and, particularly, sodium and potassium) cation, with appropriate stoichiometric adjustments being made in view of charges of the ions.

The skilled person will recognize that, when dissolved in a suitable solvent (e.g. water) the pharmaceutically acceptable salt (e.g. alkali metal salt, alkaline earth metal salt or quaternary ammonium salt) of the compound of formula I may dissociate into its anionic and cationic components.

Pharmaceutically acceptable salts of the compound of formula I may be prepared in accordance with techniques that are well known to those skilled in the art. For example, the compound of formula I may be reacted with the appropriate alkali metal hydroxide, or an alternative alkali metal base compound. Salt switching techniques may also be used to convert one salt into another salt.

In particular embodiments, the pharmaceutically acceptable salt is a sodium or potassium salt of the compound of formula I. Preferably, the pharmaceutically acceptable salt is the sodium salt.

The compounds disclosed herein may exist in unsolvated as well as solvated forms with pharmaceutically acceptable solvents such as water and ethanol, and it is intended that the invention embraces both solvated and unsolvated forms of the compounds of the invention.

The term "solvate" refers to a complex of variable stoichiometry formed by a solute and solvent. Such solvents for the purpose of the invention may not interfere with the biological activity of the solute. Examples of suitable solvents include, but are not limited to, water, methanol, ethanol, and acetic acid. Solvates in which water is the solvent molecule are typically referred to as hydrates. Hydrates include compositions containing stoichiometric amounts of water, as well as compositions containing variable amounts of water.

Compounds of formula I contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

The present invention also embraces isotopically-labelled compounds of formula I which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the invention. Hence, the compounds of formula I also include deuterated compounds, i.e. compounds of formula I in which one or more hydrogen atoms are replaced by the hydrogen isotope deuterium.

Throughout this specification, structures may or may not be presented with chemical names. Where any question arises as to nomenclature, the structure prevails. Where it is possible for the compound to exist as a tautomer (e.g. in an alternative resonance form) the depicted structure represents one of the possible tautomeric forms, wherein the actual tautomeric form(s) observed may vary depending on environmental factors such as solvent, temperature or pH. All tautomeric (and resonance) forms and mixtures thereof are included within the scope of the invention.

Unless indicated otherwise, all technical and scientific terms used herein will have their common meaning as understood by one of ordinary skill in the art to which this invention pertains.

For the avoidance of doubt, the skilled person will understand that references herein to particular aspects of the invention (such as the first aspect of the invention) will include references to all embodiments and particular features thereof, which embodiments and particular features may be taken in combination to form further embodiments and features of the invention.

In particular embodiments, the compound of formula I is Compound 3:

Compound 3

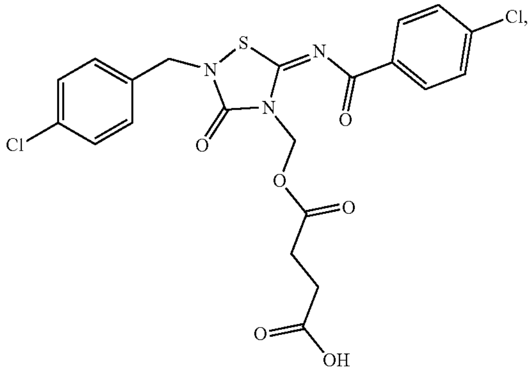 [SMILES: O=C(O)CCC(=O)OCn1c(=O)n(Cc2ccc(Cl)cc2)s/c1=N/C(=O)c1ccc(Cl)cc1]

or a pharmaceutically acceptable salt or solvate thereof. Compound 3 is known as 4-({(5Z)-5-[(4-chlorobenzoyl) imino]-2-[(4-chlorophenyl)methyl]-3-oxo-1,2,4-thiadiazolidin-4-yl}methoxy)-4-oxobutanoic acid. In a further embodiment, the compound of the invention is a sodium salt of Compound 3.

In other embodiments, the compound of formula I is Compound 5A:

Compound 5A

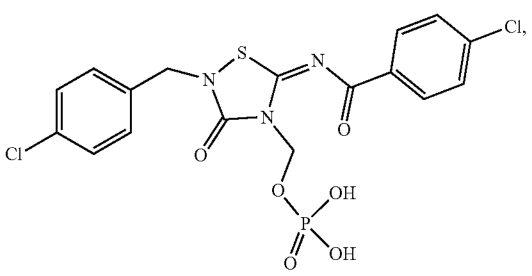 [SMILES: O=C(/N=c1/sn(Cc2ccc(Cl)cc2)c(=O)n1COP(=O)(O)O)c1ccc(Cl)cc1]

or a pharmaceutically acceptable salt or solvate thereof. Compound 5A is known as {(5Z)-5-[(4-chlorobenzoyl) imino]-2-[(4-chlorophenyl)methyl]-3-oxo-1,2,4-thiadiazolidin-4-yl}methyl phosphoric acid. In a further embodiment, the compound of the invention is a sodium salt of Compound 5A, particularly disodium {(5Z)-5-[(4-chlorobenzoyl) imino]-2-[(4-chlorophenyl)methyl]-3-oxo-1,2,4-thiadiazolidin-4-yl}methyl phosphate (referred to herein as "Compound 5").

The compounds of the invention may be considered to be prodrugs of 4-chloro-N-[2-[(4-chlorophenyl)methyl]-3-oxo-1,2,4-thiadiazol-5-yl]benzamide as they have been found to break down in vivo to form said compound. 4-Chloro-N-[2-[(4-chlorophenyl)methyl]-3-oxo-1,2,4-thiadiazol-5-yl] benzamide maybe depicted as the compound of formula II

II

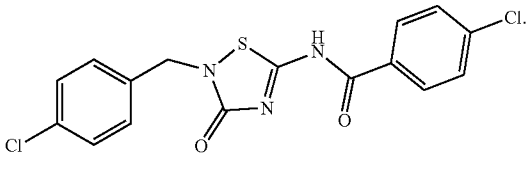

The term "prodrug" refers to a compound that, following oral or parenteral administration, is metabolised in vivo to yield a pharmalogically active compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration. General information on prodrugs may be found e.g. in Bundegaard, H. "Design of Prodrugs" p. 1-92, Elsevier, New York-Oxford (1985).

It has been found that administration of the compounds of the invention surprisingly resulted in a significant increase in the bioavailability and systemic exposure of 4-chloro-N-[2-[(4-chlorophenyl)methyl]-3-oxo-1,2,4-thiadiazol-5-yl]benzamide as compared to the bioavailability and systemic exposure observed following administration of 4-chloro-N-[2-[(4-chlorophenyl)methyl]-3-oxo-1,2,4-thiadiazol-5-yl] benzamide.

The bioavailability of a drug is the amount of an administered dose that reaches the systemic circulation in that drug form. Sufficient bioavailability is important to achieve a therapeutically active concentration at the site of action. An improvement (i.e. an increase) in bioavailability may be demonstrated by measuring the $C_{max}$ or the area under the curve (AUC) in the blood of a subject following administration of the compound (or pharmaceutical formulation thereof) to that subject. The compounds and formulations of the invention are useful in the therapies described herein in a subject in need of such therapy. Subjects that may be mentioned include animals, such as mammals. Particular mammals that might be mentioned include, for example, primates (e.g., humans, male or female), cows, horses, dogs and cats. Preferably the subject is a human.

The terms "$C_{max}$" and "AUC" will be well understood by the person skilled in the art to refer, in the present context, to the peak plasma concentration of 4-chloro-N-[2-[(4-chlorophenyl)methyl]-3-oxo-1,2,4-thiadiazol-5-yl]benzamide after administration (e.g. to a human subject) and the integral of the concentration/time curve for that substance following the administration of the compound of the invention (or formulation thereof), respectively.

It has been found that administration of a compound of the invention resulted in a particularly enhanced bioavailability of 4-chloro-N-[2-[(4-chlorophenyl)methyl]-3-oxo-1,2,4-thiadiazol-5-yl]benzamide in vivo, as is evidenced by the data in the examples. These data show that plasma exposure of 4-chloro-N-[2-[(4-chlorophenyl)methyl]-3-oxo-1,2,4-thiadiazol-5-yl]benzamide is increased when said compound is administered to a mammalian subject as compared to the plasma exposure observed following administration of 4-chloro-N-[2-[(4-chlorophenyl)methyl]-3-oxo-1,2,4-thiadiazol-5-yl]benzamide.

Thus, administration of the compounds of the invention is capable of increasing the bioavailability of 4-chloro-N-[2-[(4-chlorophenyl)methyl]-3-oxo-1,2,4-thiadiazol-5-yl]benzamide compared to administration of 4-chloro-N-[2-[(4-chlorophenyl)methyl]-3-oxo-1,2,4-thiadiazol-5-yl] benzamide. In this context, the phrase "increasing the bioavailability" means that administration of the compound of the invention results in a larger systemically available fraction of 4-chloro-N-[2-[(4-chlorophenyl)methyl]-3-oxo-1,2,4-thiadiazol-5-yl]benzamide in vivo compared to administration of 4-chloro-N-[2-[(4-chlorophenyl)methyl]-3-oxo-1,2,4-thiadiazol-5-yl]benzamide. The increase in the systemically available fraction of 4-chloro-N-[2-[(4-chlorophenyl)methyl]-3-oxo-1,2,4-thiadiazol-5-yl]benzamide may be at least about 10%, (at least) about 20%, about 30%, about 40%, about 50%, about 60%, about 70%, about 80%, about 90%, about 100% (i.e. 2-fold), about 150%, about 200% (i.e. 3-fold), about 250%, about 300% (i.e. 4-fold), about 350%, or about 400% (i.e. 5-fold).

The improvement of the bioavailability provided by the compounds of the invention may be demonstrated using suitable methods known in the art. For example, the improvement in bioavailability may be demonstrated by comparing the pharmacokinetic data (e.g. AUC data) for a subject who has been administered a compound of the invention with the corresponding data for a subject who has been administered 4-chloro-N-[2-[(4-chlorophenyl)methyl]-3-oxo-1,2,4-thiadiazol-5-yl]benzamide.

As indicated by the examples, the compounds of the invention have comparable stability to 4-chloro-N-[2-[(4-chlorophenyl)methyl]-3-oxo-1,2,4-thiadiazol-5-yl]benzamide in mildly basic solutions (e.g. at pH 7.4). Thus, the compounds of the invention are suited to being prepared into pharmaceutical formulations for administration to patients. However, both the compounds of the invention and Compound of Formula II show reduced stability under acidic condition so decomposition in the stomach environment is likely unless adequate protection is provided for orally administered formulations.

The compounds of the invention have also been found to be surprisingly effective at activating AMPK, as is evidenced by the data in the examples. As AMPK activators (i.e. AMPK agonists), the compounds of the invention may be useful in the treatment of disorders or conditions which are ameliorated by the activation of AMPK. Such compounds may therefore be useful in the treatment of the particular diseases described herein.

The compounds of the invention may be prepared from 4-chloro-N-[2-[(4-chlorophenyl)methyl]-3-oxo-1,2,4-thiadiazol-5-yl]benzamide. 4-Chloro-N-[2-[(4-chlorophenyl)methyl]-3-oxo-1,2,4-thiadiazol-5-yl]benzamide may, in turn, be prepared in accordance with techniques that are well known to those skilled in the art. For example, 4-chloro-N-[2-[(4-chlorophenyl)methyl]-3-oxo-1,2,4-thiadiazol-5-yl]benzamide may be made in accordance with the techniques described in international patent application WO 2011/004162, and all of its content is hereby incorporated by reference.

Compounds of the invention as described herein may be prepared in accordance with techniques that are well known to those skilled in the art, such as those described in the examples provided hereinafter.

Compounds of formula I may be obtained by analogy with the processes known in the literature, or by conventional synthetic procedures, in accordance with standard techniques, from available starting materials using appropriate reagents and reaction conditions. In this respect, the skilled person may refer to inter alia "Comprehensive Organic Synthesis" by B. M. Trost and I. Fleming, Pergamon Press, 1991.

For example, there is provided a process for the preparation of a compound of the invention as hereinbefore defined, which process comprises:

(i) reaction of a compound of formula V,

V

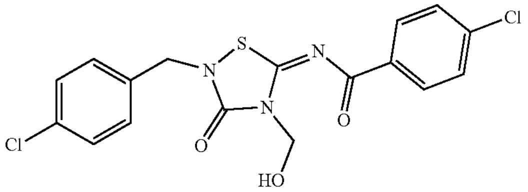

with a suitable acid or acid anhydride (e.g. succinic anhydride) in the presence of a suitable base (e.g. 4-dimethylaminopyridine) and a suitable solvent (e.g. tetrahydrofuran) according to procedures know to the person skilled in the art; or (ii) reaction of a compound of formula VI,

VI

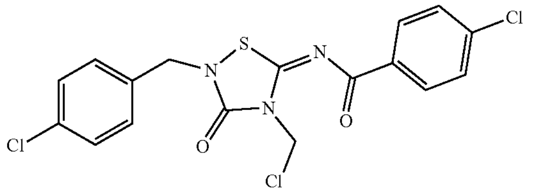

with a suitable acid or suitable acid salt (e.g. phosphoric acid, optionally presented as an ammonium dihydrogen phosphate) in the presence of a suitable base (e.g. 4-tributylamine) and a suitable solvent (e.g. dichloromethane) according to procedures know to the person skilled in the art.

The compound of formula V may be obtained by conventional synthetic procedures, in accordance with standard techniques, from available starting materials using appropriate reagents and reaction conditions. For example, the compound of formula V may be prepared by reaction of a compound of formula II,

II

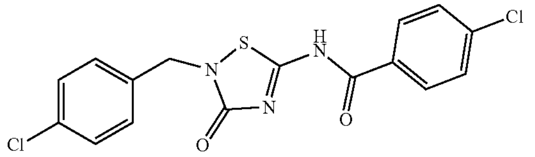

with formaldehyde in the presence of a suitable base (e.g. triethylamine) and a suitable solvent (e.g. N,N-dimethylformamide) according to procedures know to the person skilled in the art.

Similarly, the compound of formula VI may also be obtained by conventional synthetic procedures, in accordance with standard techniques, from available starting materials using appropriate reagents and reaction conditions. For example, the compound of formula VI may be prepared by reaction of a compound of formula V with a chlorinating agent (e.g. thionyl chloride) according to procedures know to the person skilled in the art.

Likewise, the compound of formula II (i.e. 4-chloro-N-[2-[(4-chlorophenyl)methyl]-3-oxo-1,2,4-thiadiazol-5-yl]benzamide; referred to in the examples as Compound 1) may be prepared in accordance with techniques that are well known to those skilled in the art, e.g. the techniques described in international patent application no. WO 2011/004162.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

Pharmaceutical Formulations

As indicated herein, the compounds of the invention are useful as therapeutic agents for treating a variety of medical disorders or conditions. Typically, compounds of the invention will be administered to a subject in need thereof in the form of a pharmaceutical formulation.

According to a second aspect of the invention, there is provided a pharmaceutical formulation comprising the compound of formula I (or a pharmaceutically acceptable salt or solvate thereof). Such formulations are referred to herein as the formulations of the invention. All embodiments and particular features thereof described herein in respect of the first aspect of the invention are disclosed herein in respect of the second aspect of the invention.

The pharmaceutical formulations of the second aspect of the invention may be prepared in accordance with standard and/or accepted pharmaceutical practice.

In an embodiment of the second aspect of the invention, the compound of the invention (or the pharmaceutically acceptable salt or solvate thereof) is the sole active pharmaceutical ingredient present in the formulation. In a further embodiment of the second aspect of the invention, the compound of the invention (or a pharmaceutically acceptable salt or solvate thereof) is present in the formulation alongside one or more other active pharmaceutical ingredients, or may be administered as part of a combination therapy with one or more other active pharmaceutical ingredients.

The formulations of the second aspect of the invention will generally be provided as a mixture comprising the compound of the invention (or a pharmaceutically acceptable salt or solvate thereof) and one or more pharmaceutically acceptable excipients. The one or more pharmaceutically acceptable excipients may be selected with due regard to the intended route of administration in accordance with standard pharmaceutical practice. Such pharmaceutically acceptable excipients are preferably chemically inert to the active compound and preferably have no detrimental side effects or toxicity under the conditions of use. Suitable pharmaceutical formulations may be found in, for example, Remington The Science and Practice of Pharmacy, 19th ed., Mack Printing Company, Easton, Pennsylvania (1995). A brief review of methods of drug delivery may also be found in e.g. Langer, Science 249, 1527 (1990).

It has been found that pH modifying excipients are particularly advantageous in the formulations of the invention. pH modifying excipients are those which substantially alter the pH of an aqueous solution of a formulation compared to the pH of an aqueous solution of the same formulation that does not otherwise comprise said excipients. A pH modifying excipient may raise (or lower) the pH of an aqueous solution of a formulation (e.g. to a pH of 8 or more) compared to an aqueous solution of the same formulation that does not comprise said excipient. Such excipients may be useful for increasing (i.e. improving) the aqueous solubility and/or stability of the compound of the invention in the formulation.

In the formulations of the invention, it has been found that basic excipients are useful in combination with the compounds of the inventions, particularly with Compound 5 and other salts thereof, and result in an improvement in the solubility of the compound. Thus, in particular embodiments of the second aspect of the invention, the at least one pharmaceutically acceptable excipient is a basic excipient.

As used herein, the term "basic excipient" refers to a pharmaceutically acceptable excipient that increases the microenvironmental pH of the formulation. Modulation of the microenvironmental pH of a formulation has been found to improve the dissolution of the active ingredient in the formulation, which in turn may lead to enhanced oral absorption of the active ingredient. Particular basic excipients that may be mentioned include magnesium oxide, sodium hydrogen carbonate, potassium hydrogen carbonate, sodium carbonate, potassium carbonate, magnesium carbonate and calcium carbonate. In particular embodiments, the basic excipient is magnesium oxide.

Other pharmaceutically acceptable excipients may also be present in the formulation of the invention (either in addition to said basic excipient or in the absence of such an excipient). For example, formulations of the invention may contain a lubricant, a binder, a filler, a surfactant, a diluent, an anti-adherent, a coating, a flavouring, a colourant, a glidant, a preservative, a sweetener, a disintegrant, an adsorbent, a buffering agent, an antioxidant, a chelating agent, a dissolution enhancer, a dissolution retardant and/or a wetting agent.

Particular pharmaceutically acceptable excipients that may be mentioned include microcrystalline cellulose, lactose monohydrate, crospovidone, magnesium stearate, colloidal silicon dioxide, anhydrous lactose, dicalcium phosphate, mannitol, pregelatinised starch, hydroxypropyl cellulose, povidone, low-substituted hydroxypropyl cellulose, croscarmellose sodium, sodium starch glycolate, sodium stearyl fumarate, talc, hydroxypropyl methylcellulose, polysorbate 80, sodium lauryl sulphate, poloxamer 188, poloxamer 407, propylene glycol, titanium dioxide, hypromellose phthalate, hypromellose acetate succinate, methacrylic acid, methyl methacrylate copolymer, Opadry® I, Opadry® II.

In the preparation of a pharmaceutical formulation of the compounds of the invention for oral administration, the compounds of the invention may be mixed, either together or separately, with one or more of the pharmaceutical excipients (including basic excipients) listed above.

Mixtures of a compound of the invention and one or more pharmaceutically acceptable excipients may be processed into pellets or granules, or compressed into tablets. Thus, pharmaceutical formulations of the invention include formulations that are provided in the form of a tablet, mini-tablets, blocks, pellets, particles, granules or a powder for oral administration. Mixtures of a compound of the invention and one or more pharmaceutically acceptable excipients may also be provided in a form that is suitable for subcutaneous or intramuscular delivery, such as an injectable solution or a freeze-dried powder suitable for reconstitution in a suitable fluid prior to administration.

The skilled person will understand that formulations described herein may act systemically, and may therefore be administered accordingly using suitable techniques known to those skilled in the art. Formulations as described herein will normally be administered orally, subcutaneously or intramuscularly in a suitable pharmaceutically acceptable dosage form. The pharmaceutical formulation of the second aspect of the invention is preferably an oral pharmaceutical formulation.

Formulations of the invention may be prepared for oral administration in the form of a capsule. For example, capsules such as soft gelatin capsules may be prepared containing the compound of the invention alone (or a pharmaceutically acceptable salt or solvate thereof), optionally together with a suitable vehicle, e.g. vegetable oil, fat etc. Similarly, hard gelatin capsules may contain the compound of the invention alone (or a pharmaceutically acceptable salt or solvate thereof) alone, or in combination with solid powdered ingredients such as a disaccharide (e.g. lactose or saccharose), an alcohol sugar (e.g. sorbitol or mannitol), a vegetable starch (e.g. potato starch or corn starch), a polysaccharide (e.g. amylopectin or cellulose derivatives) or gelling agent (e.g. gelatin).

Particular pharmaceutical formulations of the invention include formulations that may be mentioned are those provided in the form of a capsule or a tablet, e.g. for oral administration.

Preparations intended for oral administration may further comprise an enteric coating in order to prevent or minimise dissolution or disintegration in the gastric environment. As such, oral preparations (e.g. capsules or tablets) coated with an enteric coating may provide targeted release of the compound of the invention (or a pharmaceutically acceptable salt or solvate thereof) alone in the small intestine. For example, the enteric coating may be present on the surface of the formulation (e.g. on the surface of a tablet or a capsule). Thus, in particular embodiments, the formulation further comprises an enteric coating.

It may be desirable to minimise dissolution or disintegration of a capsule or a tablet (and the like) in the gastric environment and/or provide targeted release of the active ingredient in the small intestine. Thus, in particular embodiments, the enteric coating is present on said capsule or tablet. For example, said coating may be provided as an outer layer on said capsule or tablet.

The term "enteric coating" refers to a substance (e.g. a polymer) that is incorporated into an oral medication (e.g. applied onto the surface of a tablet or a capsule) and that inhibits dissolution or disintegration of the medication in the gastric environment. Enteric coatings are typically stable at the highly acidic pH found in the stomach, but break down rapidly in higher pH of the small intestine. Therefore, enteric coatings prevent release of the active ingredient in the medication until it reaches the small intestine.

Any enteric coating known to the skilled person may be used in the present invention. Particular enteric coating materials that may be mentioned include those which comprise a substance selected from the group consisting of beeswax, shellac, an alkylcellulose polymer resin (e.g. ethylcellulose polymers, carboxymethylethylcellulose, or hydroxypropyl methylcellulose phthalate) or an acrylic polymer resin (e.g. acrylic acid and methacrylic acid copolymers, methyl methacrylate copolymers, ethoxyethyl methacrylates, cyanoethyl methacrylate, methacrylate copolymers, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), glycidyl methacrylate copolymers), cellulose acetate phthalate, and polyvinyl acetate phthalate. A particular polyacrylic resin that may be mentioned is polyacrylic resin HB-50.

Pharmaceutical formulations that may be mentioned include those in which the compound of the invention (or a pharmaceutically acceptable salt or solvate thereof) is present in a total amount that is at least 1% (or at least 10%, at least 30% or at least 50%) by weight of the formulation and up to 99% by weight of the formulation. The weight ratio of the compound of the invention (or a pharmaceutically acceptable salt or solvate thereof) to the totality of the components (i.e. the compound of the invention and all pharmaceutical excipients, e.g. adjuvants, diluents and carriers) of the pharmaceutical formulation is at least 1:99 (or at least 10:90, at least 30:70 or at least 50:50) and up to 99:1.

A "therapeutically effective amount", an "effective amount" and a "dosage" as used herein refer to an amount of a compound of the invention (or a pharmaceutically acceptable salt or solvate thereof) that is sufficient to produce a desired clinical effect, which can be a therapeutic and/or beneficial effect. The effective amount or dosage will vary with the age or general condition of the subject (e.g. a human), the severity of the condition being treated, the particular agents administered, the duration of the treatment, the nature of any concurrent treatment, the pharmaceutically acceptable excipients used, and like factors within the knowledge and expertise of those skilled in the art. As appropriate, a "therapeutically effective amount", "effective amount" or "dosage" in any individual case can be determined by one of skill in the art by reference to the pertinent texts and literature and/or by using routine experimentation. Those skilled in the art will appreciate that the therapeutic effects need not be complete or curative, as long as some benefit is provided to the subject.

The skilled person will understand that compounds of the invention, and formulations thereof, may be administered (for example, by way of one or more preparations as described herein) at varying doses, with suitable doses being readily determined by one of skill in the art. The total dosage of the compound of the invention (or a pharmaceutically acceptable salt or solvate thereof) that is to be administered to a subject in need thereof may range from about 0.01 milligrams per day (mg/day) to about 3000 mg/day, about 0.1 mg/day to about 2000 mg/day, or about 1 mg/day to about 1000 mg/day (e.g. from about 10 mg/day to about 500 mg/day). Such dosages may be, for example, oral dosages of the formulations of the second aspect of the invention. When the compound of the invention (or a pharmaceutically acceptable salt or solvate thereof) is to be administered either intramuscularly or subcutaneously, the skilled person will recognise that the dosage should be adjusted accordingly.

When administered orally, treatment with such formulations may comprise administration of a unit dose formulation containing from about 0.01 mg to about 3000 mg of the compound of the invention, for example from about 0.1 mg to about 2000 mg, or from about 1 mg to about 1000 mg (e.g. from about 10 mg to about 500 mg), of the compound of the invention. Advantageously, treatment may comprise administration of the compound of the invention (e.g. in the form of one or more capsules containing said formulation) using a single daily dose. Alternatively, the total daily dosage of the compound of the invention may be administered in divided doses two, three or four times daily (e.g. twice daily with reference to the doses described herein, such as a dose of 100 mg, 250 mg, 500 mg or 1000 mg twice daily). The skilled physician will recognise that the dosage will vary from subject to subject.

In particular embodiments, the daily dose of the compound of the invention administered to a subject is in the range of from about 1 to about 3000 mg, preferably from about 1 to about 1000 mg.

The term "about" as used herein when referring to a measurable value such as an amount of a compound, dose, time, temperature, and the like, refers to variations of 20%, 10%, 5%, 1%, 0.5%, or even 0.1% of the specified amount. It is contemplated that, at each instance, such terms may be replaced with the notation "±10%", or the like (or by indicating a variance of a specific amount calculated based on the relevant value). It is also contemplated that, at each instance, such terms may be deleted.

For the avoidance of doubt, the dose administered to a subject, particularly a human subject, in the context of the present invention should be sufficient to effect a therapeutic response in the subject over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the subject to be treated, and the stage/severity of the disease.

In any event, the medical practitioner, or other skilled person, will be able to determine routinely the actual dosage which will be most suitable for an individual subject. The above-mentioned dosages are exemplary of the average case; there can, of course, be individual instances where higher or lower dosage ranges are merited, and such are within the scope of this invention.

Combinations and Kits-of-Parts

The skilled person will understand that treatment with compounds of the invention may further comprise (i.e. be combined with) further treatment(s) for the same condition.

In particular, compounds of the invention may also be combined with one or more other (i.e. different) therapeutic agents (i.e. agents that are not compounds of the invention) that are useful in the treatment a disorder or condition ameliorated by the activation of AMPK. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a third aspect of the invention, there is provided a combination product comprising:

(I) a compound of the invention, as hereinbefore defined (i.e. in the first aspect of the invention, including all embodiments and particular features thereof); and (II) one or more other therapeutic agents that is useful in the treatment of a disorder or condition ameliorated by the activation of AMPK (e.g. a cardiovascular disease (such as heart failure), diabetic kidney disease and the like, as described herein), wherein each of components (I) and (II) is formulated in admixture, optionally with one or more pharmaceutically acceptable excipients.

In a fourth aspect of the invention, there is provided a kit-of-parts comprising:

(a) a pharmaceutical formulation as hereinbefore defined (i.e. in the second aspect of the invention); and (b) one or more other therapeutic agents that is useful in the treatment of a disorder or condition ameliorated by the activation of AMPK (e.g. a cardiovascular disease (such as heart failure), diabetic kidney disease and the like, as described herein), optionally in admixture with one or more pharmaceutically-acceptable excipients, which components (a) and (b) are each provided in a form that is suitable for administration in conjunction (i.e. concomitantly or sequentially) with the other.

With respect to the kits-of-parts as described herein, by "administration in conjunction with" (and similarly "administered in conjunction with") we include that the respective formulations are administered, sequentially, separately or simultaneously, as part of a medical intervention directed towards treatment of the relevant condition.

Thus, in relation to the present invention, the term "administration in conjunction with" (and similarly "administered in conjunction with") includes that the two active ingredients (i.e. a compound of the invention and a further agent for the treatment of a disorder or condition ameliorated by the activation of AMPK, or compositions comprising the same) are administered (optionally repeatedly) either together, or sufficiently closely in time, to enable a beneficial effect for the patient, that is greater, over the course of the treatment of the relevant condition, than if either agent is administered (optionally repeatedly) alone, in the absence of the other component, over the same course of treatment. Determination of whether a combination provides a greater beneficial effect in respect of, and over the course of, treatment of a particular condition will depend upon the condition to be treated, but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of a disorder or condition ameliorated by the activation of AMPK, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

Other therapeutic agents useful in the treatment of a disorder or condition ameliorated by the activation of AMPK (such as heart failure, diabetic kidney disease and the like, as described herein) will be well-known to those skilled in the art. Preferably the other therapeutic agent will be selected from the group consisting of biguanide antihyperglycemic agents and sodium-glucose transport protein 2 (SGLT2) inhibitors (and pharmaceutically acceptable salts and solvates thereof).

Biguanide antihyperglycemic agents that may be mentioned include phenformin, buformin and, particularly, metformin (and pharmaceutically acceptable salts thereof). Thus, in one embodiment, a compound of the invention may be provided in combination with metformin (or a pharmaceutically acceptable salt thereof) in order to treat any of the diseases disclosed herein.

The skilled person will understand that a sodium-glucose transport protein 2 inhibitor is a substance or agent that elicits a decrease in one or more functions of sodium-glucose transport protein 2, and by "decrease in the functions of sodium-glucose transport protein 2" we include the cessation of one or more functions of sodium-glucose transport protein 2, or a reduction in the rate of a particular function. A particular function that may be fully or partially inhibited is the ability of sodium-glucose transport protein 2 to act as a glucose transporter.

In particular embodiments, the sodium-glucose transport protein 2 inhibitor is a gliflozin. Gliflozins are a known class of small-molecule sodium-glucose transport protein 2 inhibitors. Hawley et al. (Diabetes, 2016, 65, 2784-2794) and Villani et al. (Molecular Metabolism, 2016, 5, 1048-1056) have recently discussed the possible mechanisms of action of certain gliflozins. Particular gliflozins which may be mentioned include, canagliflozin, dapagliflozin, empagliflozin, ipragliflozin, tofogliflozin, sergliflozin (such as sergliflozin etabonate), remogliflozin (such as remogliflozin etabonate), ertugliflozin and sotagliflozin, and pharmaceutically acceptable salts and solvates thereof.

Medical Uses

As indicated herein, the compounds of the invention are useful as pharmaceuticals. Compounds of the invention are useful because they possess pharmacological activity, and/or are metabolised in the body following oral or parenteral administration to form a compound that possesses pharmacological activity.

Thus, according to a fifth aspect of the invention there is provided a compound of the invention, as hereinbefore defined (i.e. a compound as defined in the first aspect of the invention), or a pharmaceutical formulation, combination product or kit of parts as defined in respect of the second, third and fourth aspects of the invention, for use in medicine. For the avoidance of doubt, references to compounds as defined in the first aspect of the invention include references to compounds of formula I (including all embodiments thereof) and pharmaceutically acceptable salts and solvates thereof.

Compounds of the invention (i.e. a compound as defined in the first aspect of the invention), and formulations, combination products and kits containing the same, may be particularly useful in treating a disorder or condition ameliorated by the activation of AMP-activated protein kinase (AMPK). Thus, in a sixth aspect of the invention, there is provided a compound of the invention, or a formulation comprising said compound, for use in the treatment of a disorder or condition ameliorated by the activation of AMPK.

Similarly, there is provided the use of a compound of the invention, or a formulation comprising said compound, in the manufacture of a medicament for the treatment of a disorder or condition ameliorated by the activation of AMPK. In a further alternative sixth aspect of the invention, there is provided a method of treating a disorder or condition ameliorated by the activation of AMPK comprising administering a compound of the invention (or a formulation comprising said compound) to a subject (e.g. a human) in need thereof.

By 'activate AMPK', we mean that the steady state level of phosphorylation of the Thr-172 moiety of the AMPK-α (AMPK-alpha) subunit is increased compared to the steady state level of phosphorylation in the absence of a compound of formula I or an active metabolite thereof (e.g. 4-chloro-N-[2-[(4-chlorophenyl)methyl]-3-oxo-1,2,4-thiadiazol-5-yl] benzamide). Alternatively, or in addition, we mean that there is a higher steady state level of phosphorylation of any other proteins downstream of AMPK, such as acetyl-CoA carboxylase (ACC).

The terms "disorder or condition ameliorated by the activation of AMPK" will be understood by those skilled in the art to include cardiovascular disease (such as heart failure), diabetic kidney disease, diabetes (such as type 2 diabetes), insulin resistance, non-alcoholic fatty liver disease, non-alcoholic steatohepatitis, pain, opioid addiction, obesity, cancer, inflammation (including chronic inflammatory diseases), autoimmune diseases, osteoporosis and intestinal diseases. Other diseases or conditions that may be ameliorated by the activation of AMPK include hyperinsulinemia and associated conditions, a condition/disorder where fibrosis plays a role, sexual dysfunction and neurodegenerative diseases.

The term "cancer" will be understood by those skilled in the art to include one or more diseases in the class of disorders that is characterized by uncontrolled division of cells and the ability of these cells to invade other tissues, either by direct growth into adjacent tissue through invasion, proliferation or by implantation into distant sites by metastasis. By "proliferation" we include an increase in the number and/or size of cancer cells. By "metastasis" we mean the movement or migration (e.g. invasiveness) of cancer cells from a primary tumor site in the body of a subject to one or more other areas within the subject's body (where the cells can then form secondary tumors).

Thus, compounds of the invention may be suitable for use in the treatment of any cancer type, including all tumors (non-solid and, preferably, solid tumors, such as carcinoma, adenoma, adenocarcinoma, blood cancer, irrespective of the organ). For example, the cancer cells may be selected from the group consisting of cancer cells of the breast, bile duct, brain, colon, stomach, reproductive organs, thyroid, hematopoietic system, lung and airways, skin, gallbladder, liver, nasopharynx, nerve cells, kidney, prostate, lymph glands and gastrointestinal tract. Preferably, the cancer is selected from the group consisting of colon cancer (including colorectal adenomas), breast cancer (e.g. postmenopausal breast cancer), endometrial cancer, cancers of the hematopoietic system (e.g. leukemia, lymphoma, etc.), thyroid cancer, kidney cancer, oesophageal adenocarcinoma, ovarian cancer, prostate cancer, pancreatic cancer, gallbladder cancer, liver cancer and cervical cancer. More preferably, the cancer is selected from the group consisting of colon, prostate and, particularly, breast cancer. Where the cancer is a non-solid tumor, it is preferably a hematopoietic tumor such as a leukemia (e.g. Acute Myelogenous Leukemia (AML), Chronic Myelogenous Leukemia (CML), Acute Lymphocytic Leukemia (ALL), or Chronic Lymphocytic Leukemia (CLL). Preferably the cancer cells are breast cancer cells.

The term "diabetes" (i.e. diabetes mellitus) will be understood by those skilled in the art to refer to both type 1 (insulin-dependent) diabetes and type 2 (insulin-independent) diabetes, both of which involve the malfunction of glucose homeostasis. The compounds of the invention and formulations thereof may be particularly suitable for use in the treatment of type 1 diabetes and/or type 2 diabetes. The compounds of the invention are particularly suited for the treatment of type 2 diabetes.

As well as being useful in the treatment of diabetes, the compounds of the invention are also suitable for treating diabetic kidney disease (i.e. diabetic nephropathy). "Diabetic kidney disease" refers to kidney damage caused by diabetes and is a serious complication of type 1 diabetes and type 2 diabetes. Diabetic kidney disease affects the kidneys' ability to remove waste products from blood to be excreted as urine, and can lead to kidney failure.

Moreover, the compounds of the invention are also suitable for treating chronic kidney disease, including chronic kidney disease in the absence of type 2 diabetes. "Chronic kidney disease" is a condition characterised by a gradual loss of kidney function over time. Chronic kidney disease usually occurs as a result of one or more other diseases or conditions that affect the kidneys, such as high blood pressure, diabetes, high cholesterol, kidney infections, glomerulonephritis, polycystic kidney disease, obstruction of the urinary tract blockages in the flow of urine and long-term medication use.

The term "hyperinsulinemia or an associated condition" will be understood by those skilled in the art to include hyperinsulinemia, type 2 diabetes, glucose intolerance, insulin resistance, metabolic syndrome, dyslipidemia, hyperinsulinism in childhood, hypercholesterolemia, high blood pressure, obesity, fatty liver conditions, diabetic nephropathy, diabetic neuropathy, diabetic retinopathy, cardiovascular disease, atherosclerosis, cerebrovascular conditions such as stroke, systemic lupus erythematosus, neurodegenerative diseases such as Alzheimer's disease, and polycystic ovary syndrome. Other disease states include progressive renal disease such as chronic renal failure.

In particular, compounds of the invention and formulations thereof may be suitable for use in the treatment of obesity associated with hyperinsulinemia and/or cardiovascular disease associated with hyperinsulinemia.

Compounds of the invention and formulations thereof may also be suitable for use in the treatment of cardiovascular disease, such as heart failure, wherein said cardiovascular disease is not associated with hyperinsulinemia. Similarly, compounds of the invention and formulations thereof may also be suitable for use in the treatment of obesity which is not associated with hyperinsulinemia. For the avoidance of doubt, the treatment of obesity and/or cardiovascular disease (such as heart failure) where AMPK activation may be beneficial is included within the scope of the invention.

A condition/disorder where fibrosis plays a role includes (but is not limited to) scar healing, keloids, scleroderma, pulmonary fibrosis (including idiopathic pulmonary fibrosis), nephrogenic systemic fibrosis, and cardiovascular fibrosis (including endomyocardial fibrosis), systemic sclerosis, liver cirrhosis, eye macular degeneration, retinal and vitreal retinopathy, Crohn's/inflammatory bowel disease, post-surgical scar tissue formation, radiation and chemotherapeutic-drug induced fibrosis, and cardiovascular fibrosis.

The compounds of invention may also be useful in the treatment of sexual dysfunction (e.g. the treatment of erectile dysfunction). The compounds of invention may also be useful in the treatment of inflammation.

Neurodegenerative diseases that may be mentioned include Alzheimer's disease, Parkinson's disease and Huntington's disease, amyotrophic lateral sclerosis, polyglutamine disorders, such as spinal and bulbar muscular atrophy (SBMA), dentatorubral and pallidoluysian atrophy (DRPLA), and a number of spinocerebellar ataxias (SCA).

Compounds of the invention may be useful in the treatment of a non-alcoholic fatty liver disease (NAFLD).

Non-alcoholic fatty liver disease (NAFLD) is defined by excessive fat accumulation in the form of triglycerides (steatosis) in the liver (designated as an accumulation of greater than 5% of hepatocytes histologically). It is the most common liver disorder in developed countries (for example, affecting around 30% of US adults) and most patients are asymptomatic. If left untreated, the condition may progressively worsen and may ultimately lead to cirrhosis of the liver. NAFLD is particularly prevalent in obese patients, with around 80% thought to have the disease.

NAFLD may be diagnosed wherein alcohol consumption of the patient is not considered to be a main causative factor. A typical threshold for diagnosing a fatty liver disease as "not alcohol related" is a daily consumption of less than 20 g for female subjects and less than 30 g for male subjects.

Particular diseases or conditions that are associated with NAFLD include metabolic conditions such as diabetes, hypertension, obesity, dyslipidemia, abetalipoproteinemia, glycogen storage diseases, Weber-Christian disease, acute fatty liver of pregnancy, and lipodystrophy. Other non-alcohol related factors related to fatty liver diseases include malnutrition, total parenteral nutrition, severe weight loss, refeeding syndrome, jejunoileal bypass, gastric bypass, polycystic ovary syndrome and diverticulosis.

Non-alcoholic steatohepatitis (NASH) is the most aggressive form of NAFLD, and is a condition in which excessive fat accumulation (steatosis) is accompanied by inflammation of the liver. If advanced, NASH can lead to the development of scar tissue in the liver (fibrosis) and, eventually, cirrhosis. As described above, the compounds of the invention have been found to be useful in the treatment of NAFLD and inflammation. It follows that the compounds of the invention are also useful in the treatment of NASH. Therefore, in a further embodiments, the treatment is of non-alcoholic steatohepatitis (NASH).

It has been shown that AMPK activator compounds (such as 4-chloro-N-[2-[(4-chlorophenyl)methyl]-3-oxo-1,2,4-thiadiazol-5-yl]benzamide (i.e. the compound of formula II)) are capable of treating pain (Das V, et al. Reg Anesth Pain Med 2019; 0:1-5. doi:10.1136/rapm-2019-100839 and Das V, et al. Reg Anesth Pain Med 2019; 0:1-6. doi:10.1136/rapm-2019-100651) and such compounds may be considered to be analgesics. It therefore follows that, since the compounds of the invention are capable of activating AMPK, or are metabolised in vivo to form a known AMPK activator compound, the compounds of the invention may be useful in the treatment of pain. In particular, the compounds of the invention may be useful in the treatment of patients with severe pain, chronic pain or useful in the management of pain after surgery.

Opioid-based therapies, such as opioid analgesics, are used to treat severe, chronic cancer pain, acute pain (e.g. during recovery from surgery and breakthrough pain) and their use is increasing in the management of chronic, non-malignant pain. However, the increasing use of opioid-based therapies to treat pain has resulted in an increase of opioid dependence (e.g. opioid addiction). As AMPK activators, the compounds of the invention may be used to treat pain in place of an opioid-based therapy, as known by those skilled in the art. Accordingly, the compounds of the invention may be useful in treating opioid addiction.

Particular autoimmune diseases know to those skilled in the art include Crohn's/inflammatory bowel disease, systemic lupus erythematosus and type 1 diabetes.

Particular intestinal diseases that should be mentioned include Crohn's/inflammatory bowel disease and cancer of gastrointestinal tract.

The skilled person will understand that references to the "treatment" of a particular condition (or, similarly, to "treating" that condition) will take their normal meanings in the field of medicine. In particular, the terms may refer to achieving a reduction in the severity and/or frequency of occurrence of one or more clinical symptom associated with the condition, as judged by a physician attending a subject having or being susceptible to such symptoms.

The skilled person will understand that such treatment or prevention will be performed in a subject in need thereof. The need of a subject for such treatment or prevention may be assessed by those skilled the art using routine techniques. In the context of the present invention, a "subject in need" of the compound of the invention includes a subject that is suffering a disorder or condition ameliorated by the activation of AMPK. As used herein, the terms "disease" and "disorder" (and, similarly, the terms condition, illness, medical problem, and the like) may be used interchangeably.

Without wishing to be bound by theory, it is believed that the administration of a compound of the invention enhances the bioavailability of 4-chloro-N-[2-[(4-chlorophenyl)methyl]-3-oxo-1,2,4-thiadiazol-5-yl]benzamide in the systemic circulation. Administration of formulations comprising a compound of the invention has been shown to provide an approximately two-fold increase in the plasma concentration of 4-chloro-N-[2-[(4-chlorophenyl)methyl]-3-oxo-1,2,4-thiadiazol-5-yl]benzamide under certain circumstances compared to administration of a formulation that comprises 4-chloro-N-[2-[(4-chlorophenyl)methyl]-3-oxo-1,2,4-thiadiazol-5-yl]benzamide.

Compounds of the invention (and formulations thereof) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, other therapies known in the prior art, whether for use in the above-stated indications or otherwise. In particular, compounds of the invention may have the advantage that they are more efficacious and/or exhibit advantageous properties in vivo.

FIGURES

The following drawings are provided to illustrate various aspects of the present inventive concept and are not intended to limit the scope of the present invention unless specified herein.

EXAMPLES

Figure 1:
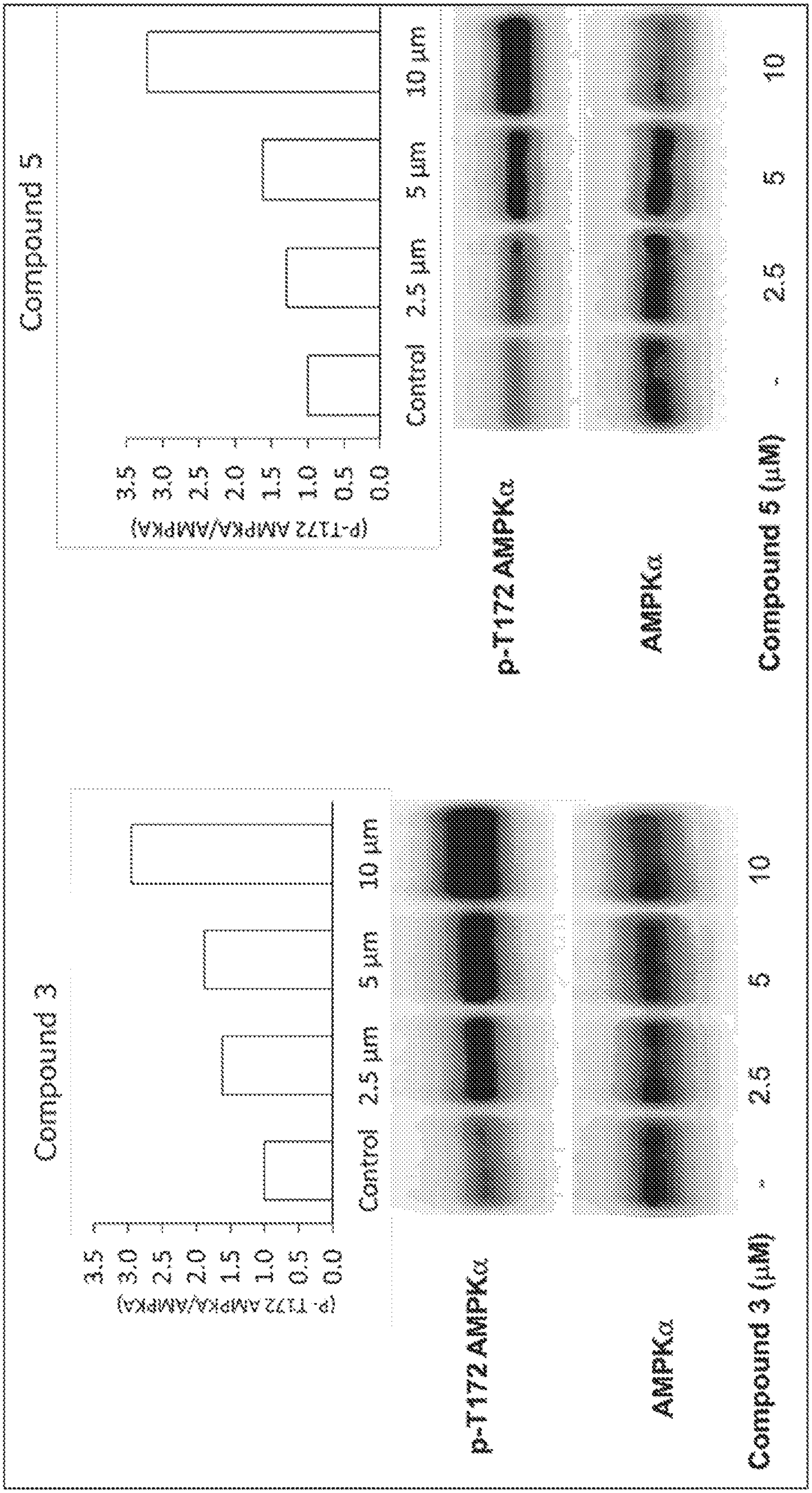
FIG. 1 shows western blot images that demonstrate that Compounds 3 and 5 increase phosphorylation of AMPK in a dose-dependent manner.

The present invention is explained in greater detail in the following non-limiting examples.

The reaction schemes described below are intended to provide a general description of the methodology employed in the preparation of the compounds of the invention. The examples provided herein are offered to illustrate but not limit the compounds of the invention, as well as the preparation of such compounds and intermediates.

All starting materials, building blocks, reagents, acids, bases, dehydrating agents, solvents and catalysts utilised to synthesise the compounds of the invention are either commercially available or can be routinely prepared by procedures described in the literature, for example, Houben-Weyl "Science of Synthesis" volumes 1-48, Georg Thieme Verlag, and subsequent versions thereof.

A reaction may be carried out in the presence of a suitable solvent or diluent or of mixture thereof in a manner known to those skilled in the art of organic synthesis. A reaction may also be carried out, if needed, in the presence of an acid or a base, with cooling or heating, for example in a temperature range from about −30° C. to about 150° C. In some embodiments, a reaction is carried out in a temperature range from about 0° C. to about 100° C., and more particularly, in a temperature range from room temperature to about 80° C., in an open or closed reaction vessel and/or in the atmosphere of an inert gas, for example nitrogen.

Abbreviations

Abbreviations as used herein will be known to those skilled in the art. In particular, the following abbreviations may be used herein.

AUC: Area under the concentration-time curve
aq: Aqueous
b.w.: Body weight
$C_{max}$: Peak plasma concentration
d: Doublet
DCM: Dichloromethane
DMF: Dimethylformamide
DMAP: 4-Dimethylaminopyridine
DMSO: Dimethylsulfoxide
ESI: Electrospray ionisation
$Et_3N$: Triethylamine
EtOH: Ethanol
g: Gram
h: Hours
HPLC: High performance liquid chromatography
LC: Liquid chromatography
LCMS: Liquid chromatography—mass spectrometry
LC-MS/MS: Liquid chromatography—(tandem) mass spectrometry
LLOQ: Lower limit of quantification
m: Multiplet
MeOD: Methanol-$d_4$
Min: Minutes
mL: Millilitre
MRT: Mean residence time
$nBu_3N$: Tributylamine
ND: Not detected
NMR: Nuclear magnetic resonance
RT: Room temperature
s: Singlet
$T_{1/2}$: Half-life
$T_{max}$: Time to reach the peak plasma concentration
THF: Tetrahydrofuran
TLC: Thin-layer chromatography

Instrumentation Conditions

LC Parameters

Column: Agilent Zorbax SB-C8, 50×4.6 mm, 350 μm
Mobile phase: 5 mM ammonium acetate:methanol with 0.1% formic acid (15:85 v/v)
Separation mode: Isocratic
Flow rate: 0.800 mL/min
Injection volume: 2 μL
Auto sampler temperature: 4° C.
Column oven temperature: 40° C.
LC-MS/MS Shimadzu LCMS-8045
Source ESI
Polarity Positive
m/z of analyte (Compound 1) 379.800>89.100
m/z of internal standard (warfarin) 309.100>251.100

The present invention will be further described by reference to the following examples, which are not intended to limit the scope of the invention.

Example 1: preparation of 4-({(5Z)-5-[(4-chlorobenzoyl)imino]-2-[(4-chlorophenyl)methyl]-3-oxo-1,2,4-thiadiazolidin-4-yl}methoxy)-4-oxobutanoic Acid

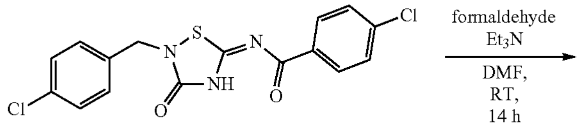

1

-continued

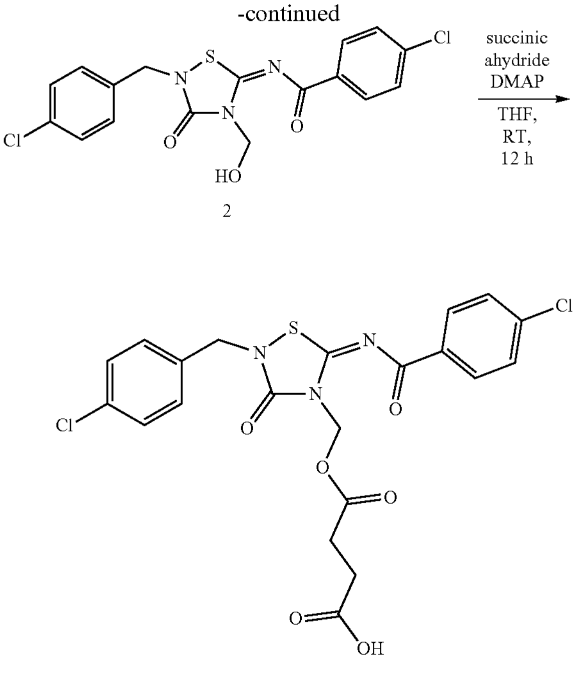

2

3

Compound 1: 4-choro-N-[2-[(4-chlorophenyl) methyl]3-oxo-1,2,4-thiadiazol-5-yl]benzamide Compound 1 was prepared in accordance with the procedures described in WO 2011/004162.

Compound 2: 4-choro-N-{2-[(4-chlorophenyl) methyl]-4-(hydroxymethyl)-3-oxo-1,2,4-thiadiazolidin-5-ylidene}-benzamide To a stirring solution of Compound 1 (10 g, 0.026 mol) in DMF (200 mL) were added $Et_3N$ (15 mL, 0.105 mol) and 37% formaldehyde (8.5 mL, 0.105 mol). The reaction mixture was stirred at RT for 12 to 14 h.

The reaction mixture was then concentrated to remove the DMF. The crude material obtained was slurried in water (100 mL) for 30 minutes. The slurry was filtered and dried at ambient temperature to yield Compound 2 as white solid (9.6 g, 90.5% yield).

Compound 3: 4-({(5Z)-5-[(4-chlorobenzoyl)imino]-2-[(4-chlorophenyl)methyl]-3-oxo-1,2,4-thiadiazolidin-4-yl}methoxy)-4-oxobutanoic Acid To a stirring solution of Compound 2 (10 g, 0.024 mol) in THF (200 mL) were added DMAP (0.44 g, 0.004 mol) and succinic anhydride (7.29 g, 0.072 mol). The reaction mixture was stirred at RT for 12 h.

After completion (as observed by TLC), the reaction mixture was concentrated to remove the THF. The crude material obtained was diluted with THF (100 mL), stirred for 1 h at RT and filtered to afford Compound 3 as a white solid (7.3 g, 59% yield).

$^1$H NMR (300 MHz, MeOD) δ (ppm): 2.61 (m, 4H), 4.72 (s, 2H), 6.10 (s, 2H), 7.29 (dd, 4H), 7.41 (d, 2H), 8.12 (d, 2H).

LCMS: 510.4 [M+H].

HPLC: >98% purity at 13.6 minutes.

Example 2: preparation of disodium {(5Z)-5-[(4-chlorobenzoyl)imino]-2-[(4-chlorophenyl)methyl]-3-oxo-1,2,4-thiadiazolidin-4-yl}methyl Phosphate

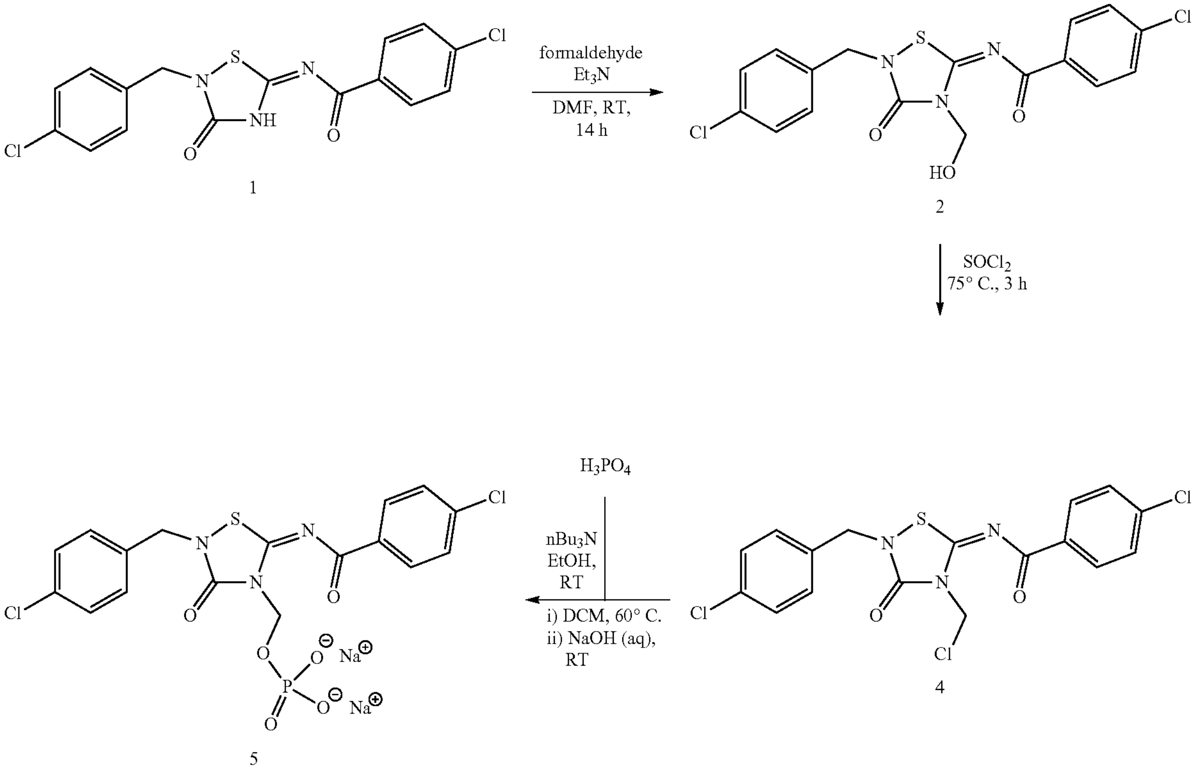

1

2

4

5

Compound 2: 4-choro-N-{2-[(4-chlorophenyl) methyl]-4-(hydroxymethyl)-3-oxo-1,2,4-thiadiazolidin-5-ylidene}benzamide Compound 2 was prepared in accordance with the procedure described in Example 1.

Compound 4: 4-chloro-N-{4-(chloromethyl)-2-[(4-chlorophenyl)methyl]-3-oxo-1,2,4-thiadiazolidin-5-ylidene}benzamide A mixture of Compound 2 (10 g, 0.0243 mol) and thionyl chloride (60 mL) was heated to 75° C. over a period of 3 h.

After completion (as observed by TLC), the reaction mixture was concentrated and the crude product was washed with diethyl ether (3×100 mL) to afford Compound 4 as a white solid (9.5 g, 90% yield).

Compound 5: disodium {(5Z)-5-[(4-chlorobenzoyl) imino]-2-[(4-chlorophenyl)methyl]-3-oxo-1,2,4-thiadiazolidin-4-yl}methyl Phosphate To a stirring solution of phosphoric acid (85%, 15.1 g, 0.154 mol) in ethanol (60 mL), tributylamine (83 mL, 0.35 mol) was added at ambient temperature. The solvent was removed by evaporation and the residue was dissolved in DCM (60 mL). The DCM solution was dried over sodium sulphate, filtered and evaporated to afford di-tributyl-ammonium dihydrogen phosphate.

A mixture of Compound 4 (3.0 g, 0.007 mol) and the above prepared tributyl-ammonium dihydrogen phosphate was taken in DCM (60 mL) and stirred for 10 min. The reaction mixture was distilled off at 40° C. and the residue obtained was heated at 60° C. on a water bath for 10 to 15 minutes. The residue was re-dissolved in DCM (6 mL), the DCM was distilled off and residue obtained was heated at 60° C. on a water bath for 10 to 15 min. The above procedure was repeated for four times.

After completion (as observed by TLC), the residue was dissolved in DCM (4 mL) and washed with water (3×4 mL). The organic phase was separated, dried over sodium sulphate, filtered and concentrated. The crude product obtained upon evaporation was taken in water and basified (pH 9 to 9.5) with 0.2 M sodium hydroxide. After basification, the mixture was filtered and filtrate was lyophilized to yield Compound 5 as a white solid (0.6 g, 17.5% yield).

$^1H$ NMR (300 MHz, DMSO-$D_6$) δ (ppm): 4.78 (s, 2H), 5.55 (s, 2H), 7.40 (dd, 4H), 7.55 (d, 2H), 8.19 (d, 2H).

LCMS: 490.1 [M+H].

HPLC: >98% purity at 8.2 minutes.

Example 3—Solubility of Compounds at Different pH

Methods

Approximately 5 mg of each test compound (Compounds 1 and 5) was weighed in duplicate, and each weighed sample was transferred to a separate centrifuge tube containing 5 mL of the respective buffer. All the tubes were tightly stoppered and agitated at a constant rate at 30±1° C. using an orbital shaker.

After 24 hours, one tube of each buffer solution was removed from the shaker. 50 μL of the buffer solution from each removed tube was transferred into a 10 mL tube and made up to the mark with diluent. Then 2.5 mL of the supernatant of each tube was transferred into a 50 mL tube and made up to 25 mL.

The nominal concentration of the solution in each 50 mL tube was 5 μg/mL.

Linearity solutions of 40 ng/mL to 10000 ng/mL were plotted.

Results

The results for the solubility experiments are tabulated in Tables 1 and 2 below.

The results show that Compound 5 has a higher solubility compared to Compound 1 in basic solutions (i.e. pH>7) as well as in mildly acidic conditions. In particular, Compound 5 is up to 30-times more soluble in basic solution compared to Compound 1.

TABLE 1

Results of a Two-hour Solubility Study of Compounds 1 and 5
Absolute Solubility: 2 hours incubation

| | Solubility (mg/ml) | |
|---|---|---|
| Buffer | Compound 1 | Compound 5* |
| HCl Buffer, PH: 1.20 | ND | ND |
| Acetate Buffer, pH: 4.50 | ND | 0.015 |
| Phosphate Buffer, pH: 7.40 | ND | 0.119 |
| Alkaline Borate Buffer, pH: 9.20 | 0.029 | 0.720 |
| Ultrapure water | ND | 0.419 |

Note:
ND indicates not detected, concentration was below LLOQ;
*HPLC was analysis performed for Compound 5

TABLE 2

Results of a Twenty-hour Solubility Study of Compounds 1 and 5
Absolute Solubility: 20 hours incubation

| | Solubility (mg/ml) | |
|---|---|---|
| Buffer | Compound 1 | Compound 5* |
| HCl Buffer, pH; 1.20 | ND | ND |
| Acetate Buffer, pH: 4.50 | ND | 0.015 |
| Phosphate Buffer, pH: 7.40 | ND | 0.098 |
| Alkaline Borate Buffer, PH: 9.20 | 0.044 | 1.239 |
| Ultrapure water | ND | 0.036 |

Note:
ND indicates not detected, concentration was below LLOQ;
*HPLC was analysis performed for Compound 5

Example 4—Stability of Compounds

5 μM solutions of Compounds 1, 3 and 5 in USP buffer (pH: 7.40) were prepared with 5 mM DMSO stock solutions. The solutions were incubated at 37° C. for 120 minutes, with shaking at 400 rpm using a thermomixer.

After 0, 15, 30, 60 and 120 minute intervals, aliquots of sufficient volume of the compound solutions were taken, diluted to the final concentration and analysed.

Results

The results for the stability experiments are tabulated in Table 3 below.

The results show that Compounds 3 and 5 possess comparable stability to Compound 1 in mildly basic solutions (i.e. pH=7.4).

TABLE 3

| Comparative Stability Data in Phosphate Buffer (pH: 7.40) | | | | | |
|---|---|---|---|---|---|
| | % remaining compared to 0.0 min | | | | |
| Test Compound | 0.0 min | 15 min | 30 min | 60 min | 120 min |
| Compound 1 | 100.00 | 97.62 | 101.31 | 99.41 | 106.18 |
| Compound 3 | 100.00 | 86.96 | 93.61 | 88.74 | 75.40 |
| Compound 5 | 100.00 | 103.92 | 107.58 | 107.88 | 97.30 |

Example 5—Activation of AMPK

Cultivation and Compound Treatment of INS-1E Insulinoma Cells

INS-1E cells were cultivated as described in Steneberg et al., JCI Insight. 2018; 3(12):e99114. https://doi.org/10.1172/jci.insight.99114, using 5% instead of 10% fetal bovine serum when plated for treatment.

Compound 3 was dissolved at 10 mM in DMSO and frozen at −20° C.

Compound 5 was dissolved at 10 mM in a 50:50 water/DMSO mixture, incubated for 15 minutes at room temperature in ultrasonic bath (VWR ultrasonic cleaner), and stored at room temperature.

The INS-1E cells were treated in serum free medium with increasing doses of Compounds 3 and 5 for 4 and 16 hours, respectively, in accordance with the methods described in Steneberg et al., JCI Insight. 2018; 3(12):e99114. https://doi.org/10.1172/jci.insight.99114.

Western Blot Analysis

Western blot analysis of the INS-1E cells was performed as described in Steneberg et. al., JCI Insight. 2018; 3(12):e99114. https://doi.org/10.1172/jci.insight.99114. The cell lysates were passed through a 30-gauge needle, ~8-times and centrifuged for 10 min at +4° C. at 14000 rpm. Quantified values for AMPKα, and phosphorylated-T172 AMPKα, were normalized toward the quantified values for β-Actin.

Results

The results for Western blot analysis are tabulated in Table 3 below and are shown graphically in FIG. 1.

The results show that Compounds 3 and 5 increase phosphorylated-T172 AMPK in a dose-dependent manner in cultured INS-1E cells. Compounds 3 and 5 are therefore agonists of AMPK.

TABLE 4

| The ratio between p-T172 AMPK and non-phosphorylated AMPK | | | | | |
|---|---|---|---|---|---|
| Compound | Time | Control | 2.5 μM | 5 μM | 10 μM |
| 3 (0.1% DMSO) | 4 h | 1.00 | 1.62 | 1.88 | 2.95 |
| 5 (0.05% DMSO) | 16 h | 1.00 | 1.29 | 1.62 | 3.21 |

Example 6—Single Dose Oral Pharmacokinetic Study of Compounds 1 and 3 in Sprague Dawley Rats

Formulation of Compound 1

10.0 mL of 2% w/v methyl cellulose solution in phosphate buffer (pH 7.5) was added to a 100 mL conical flask along with 1 g of 2 mm glass beads. The solution was vigorously stirred on a magnetic stirrer. 100 mg of Compound 1 was slowly added to the solution, and the solution was vigorously stirred for approximately 1 h. The pH of the formulation was measured to be 7.49. Each formulation was freshly prepared prior to administration to the animals. The final concentration of Compound 1 in of the formulation was 10 mg/mL. The formulation was administered at 5 mL/kg body weight.

Formulation of Compound 3

10.0 mL of 2% w/v methyl cellulose solution in phosphate buffer (pH 7.5) was added to a 100 mL of conical flask together with 1 g of 2 mm glass beads. The solution was vigorously stirred on a magnetic stirrer. 134 mg of Compound 3 was slowly added to the solution, and the solution was vigorously stirred for approximately 1 h. The pH of the formulation was measured to be 7.44. Each formulation was freshly prepared prior to administration to the animals. The final concentration of Compound 3 in the formulation was 13.4 mg/mL, which is equivalent to 10 mg/mL of Compound 1. The formulation was administered at 5 mL/kg body weight.

Dose Selection and Justification for Selection

The doses of 50 mg/kg and 67 mg/kg b.w. for Compound 1 and Compound 3, respectively, were selected for comparison of equimolar doses.

Dose Administration

Adult healthy male Sprague Dawley rats aged 9 to 11 weeks were used for experimentation after a minimum three days of acclimatisation. Fed state animals were administered the formulation of Compound 1 or Compound 3 orally via gavage at a dose of 50 mg/kg or 67 mg/kg body weight, respectively.

Blood Sampling

Under mild isoflurane anesthesia, blood specimens were collected by retro-orbital puncture method using capillary tubes into pre-labeled tubes containing anticoagulant ($K_2$EDTA: 2 mg/mL blood) during the next 72 hours post-dosing, as detailed in Table 6. For blood sampling at multiple time points, the right and left eyes were used alternatively. Collected blood specimens were centrifuged at 6000 rpm, 4° C. for 10 minutes and the plasma samples were separated and stored at −80° C. until analysis.

Results

Figure 2:
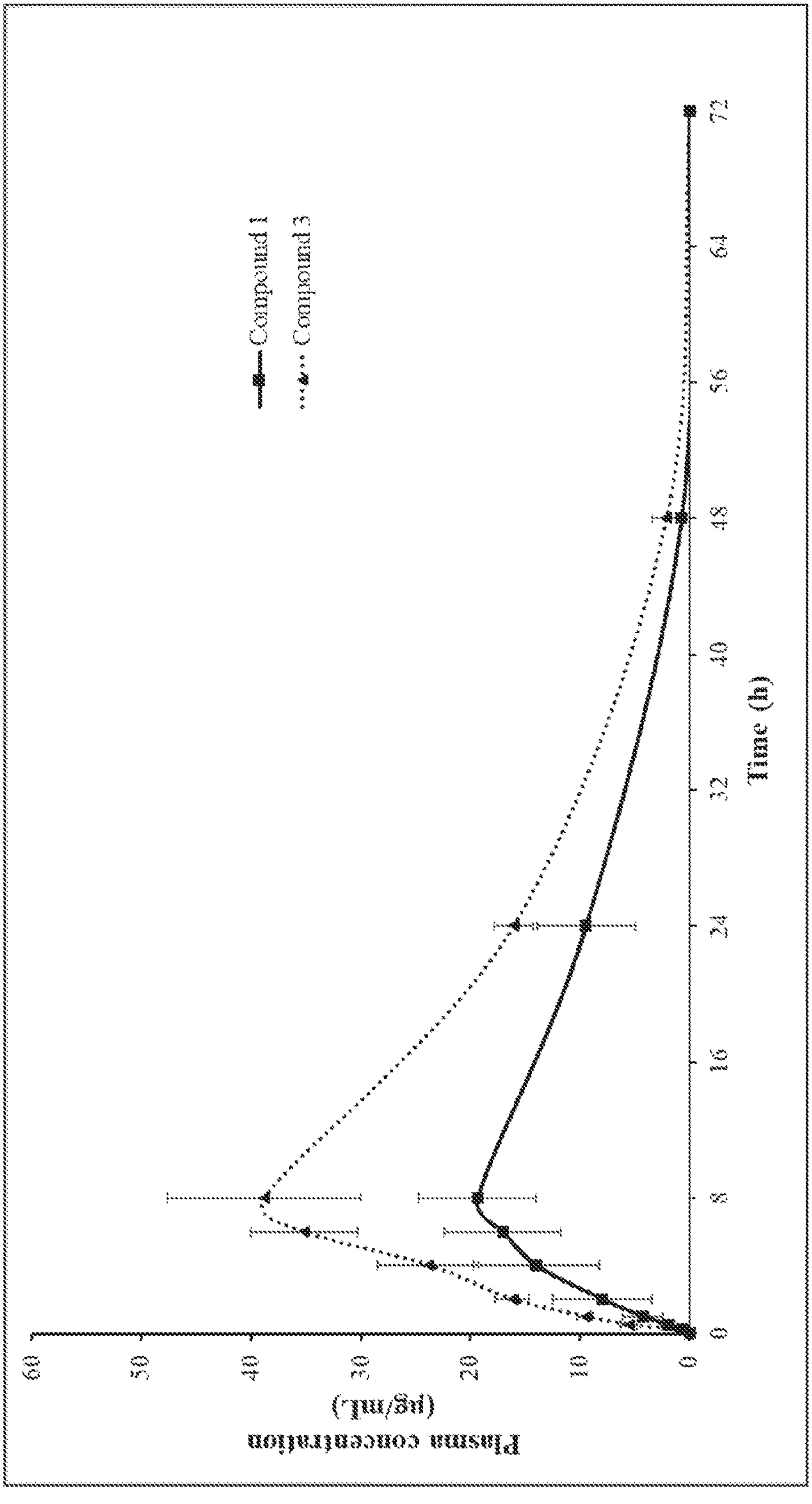
FIG. 2 shows comparative results of oral pharmacokinetic studies using Compound 1 and Compound 3.

The results for the single dose oral pharmacokinetic study in rats are tabulated in Tables 4 and 5 below and are shown graphically in FIG. 2. In Table 4, the $C_{max}$, $T_{max}$, $AUC_{last}$, $AUC_{inf}$, $AUC_{extrap}$, $T_{1/2}$ and $MRT_{last}$ values are for 4-chloro-N-[2-[(4-chlorophenyl)methyl]-3-oxo-1,2,4-thiadiazol-5-yl]

benzamide (Compound 1), which was detected following the administration of both Compounds 1 and 3.

The results show that there is a surprising two-fold increase in the systemic exposure of 4-chloro-N-[2-[(4-chlorophenyl)methyl]-3-oxo-1,2,4-thiadiazol-5-yl]benzamide when Compound 3 is administered compared to Compound 1. Thus, the systemic exposure of 4-chloro-N-[2-[(4-chlorophenyl)methyl]-3-oxo-1,2,4-thiadiazol-5-yl] benzamide is increased by administration of a compound of the invention.

TABLE 5

Mean Plasma Pharmacokinetic Parameters Following Administration of Compounds 1 and 3

| Compound No. | 1 | 3 |
|---|---|---|
| Dose (mg/kg b.w.) | 50 | 67 (equivalent to 50 of Compound 1) |
| $C_{max}$ (μg/ml) | 19.60 ± 5.54 | 40.80 ± 5.66 |
| $T_{max}$ (h) | 7.33 ± 1.16 | 7.33 ± 1.16 |
| $AUC_{last}$ (h*μg/mL) | 449.40 ± 157.75 | 847.34 ± 99.98 |
| $AUC_{inf}$ (h*μg/mL) | 458.31 ± 154.77 | 880.35 ± 91.70 |
| $AUC_{extrap}$ (%) | 2.33 ± 1.74 | 3.80 ± 3.53 |
| $T_{1/2}$ (h) | 8.42 ± 1.47 | 9.59 ± 2.96 |
| $MRT_{last}$ (h) | 14.78 ± 0.68 | 14.66 ± 1.45 |

TABLE 6

Plasma Concentration of Compounds 1 and 3

| | Plasma concentration of Compound 1 (μg/mL) | | | |
|---|---|---|---|---|
| | Compound 1 | | Compound 3 | |
| Time (h) | Mean | SD | Mean | SC |
| 0.00 | 0.00 | 0.00 | 0.00 | 0.00 |
| 0.25 | 0.62 | 0.62 | 1.13 | 0.13 |
| 0.50 | 1.98 | 0.59 | 5.53 | 0.73 |
| 1.00 | 4.24 | 1.84 | 9.51 | 0.74 |
| 2.00 | 7.99 | 4.49 | 16.17 | 1.53 |
| 4.00 | 14.01 | 5.73 | 23.83 | 4.56 |
| 6.00 | 17.00 | 5.30 | 35.17 | 4.85 |
| 8.00 | 19.33 | 5.33 | 38.83 | 8.82 |
| 24.00 | 9.44 | 4.43 | 16.03 | 1.82 |
| 48.00 | 0.72 | 0.17 | 2.12 | 1.30 |
| 72.00 | 0.00 | 0.00 | 0.00 | 0.00 |
| Lower limit of quantification of Compound 1 | | | | 0.5 μg/ml |

Example 7—Single Dose Oral Pharmacokinetic Study of Compound 5 in Sprague Dawley Rats

Formulation of Compound 5

6.0 mL of 2% w/v methyl cellulose solution in phosphate buffer (pH 7.5) was added to a 100 mL of conical flask together with 1 g of 2 mm glass beads. The solution was vigorously stirred on a magnetic stirrer. 77 mg of Compound 5 was slowly added to the solution, and the solution was vigorously stirred for approximately 1 h. The pH of the formulation was measured to be 7.43. The formulation was freshly prepared prior to administration to the animals.

Dose Administration

Adult healthy male Sprague Dawley rats aged 9 to 11 weeks were used for experimentation after a minimum three days of acclimatisation. Fed state animals were administered the formulation of Compound 5 orally via gavage at a dose of 64 mg/kg body weight (5 mL,/kg dose volume).

Blood Sampling

Under mild isoflurane anesthesia, blood specimens were collected by retro-orbital puncture method using capillary tubes into pre-labeled tubes containing anticoagulant ($K_2$EDTA: 2 mg/mL blood) during the next 72 hours post-dosing. For blood sampling at multiple time points, the right and left eyes were used alternatively. Collected blood specimens were centrifuged at 6000 rpm, 4° C. for 10 minutes and the plasma samples were separated and stored at −80° C. until analysis.

Results

The results for the single dose oral pharmacokinetic study in rats are tabulated in Tables 7 and 8 below. In Table 7, the $C_{max}$, $T_{max}$, $AUC_{last}$, $AUC_{inf}$, $AUC_{extrap}$, $T_{1/2}$ and $MRT_{last}$ values are for 4-chloro-N-[2-[(4-chlorophenyl)methyl]-3-oxo-1,2,4-thiadiazol-5-yl]benzamide (Compound 1), which was detected following the administration of Compound 5. Thus, Compound 5 acts as a prodrug of Compound 1.

TABLE 7

Mean Plasma Pharmacokinetic Parameters Following Administration of Compound 5

| Compound No. | 5 |
|---|---|
| Dose (mg/kg b.w.) | 64 |
| $C_{max}$ (μg/mL) | 30.77 ± 9.68 |
| $T_{max}$ (h) | 6.00 ± 0.0 |
| $AUC_{last}$ (h*μg/mL) | 612.21 ± 376.22 |
| $AUC_{inf}$ (h*μg/mL) | 688.74 ± 315.05 |
| $AUC_{extrap}$ (%) | 15.22 ± 14.63 |
| $T_{1/2}$ (h) | 9.09 ± 2.87 |
| $MRT_{last}$ (h) | 11.72 ± 3.69 |

TABLE 8

Plasma Concentration of Compound 1 Following Administration of Compound 5

| | Plasma concentration of Compound 1 (μg/mL) | |
|---|---|---|
| | Compound 5 | |
| Time (h) | Mean | SD |
| 0.00 | 0.00 | 0.00 |
| 0.25 | 0.84 | 0.20 |
| 0.50 | 2.39 | 0.50 |
| 1.00 | 4.78 | 1.42 |
| 2.00 | 11.09 | 2.17 |
| 4.00 | 23.97 | 10.19 |
| 6.00 | 30.77 | 9.68 |
| 8.00 | 29.23 | 10.80 |
| 24.00 | 13.84 | 10.73 |
| 48.00 | 0.23 | 0.40 |
| 72.00 | 0.00 | 0.00 |
| Lower limit of quantification of Compound 1 | | 0.5 μg/ml |

The invention claimed is:

1. A compound of formula I,

I

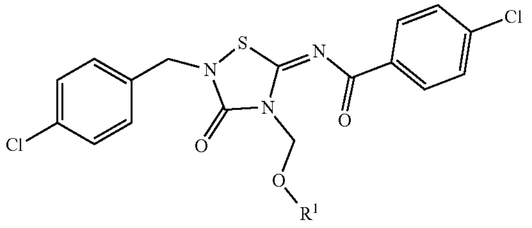

wherein $R^1$ is selected from the group consisting of $-C(O)-C_2H_4-CO_2H$ and $-PO_3H_2$, or a pharmaceutically acceptable salt or solvate thereof.

2. The compound according to claim 1, wherein the compound of formula I is:

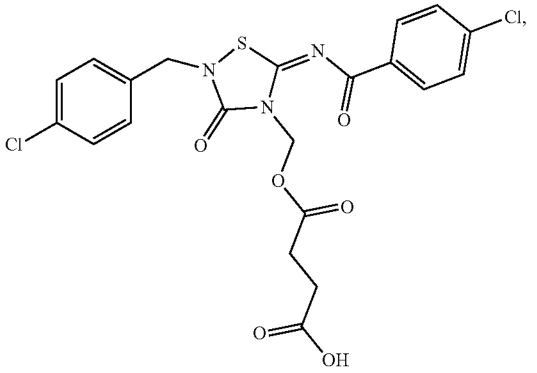

or a pharmaceutically acceptable salt or solvate thereof.

3. The compound according to claim 1, wherein the compound of formula I is:

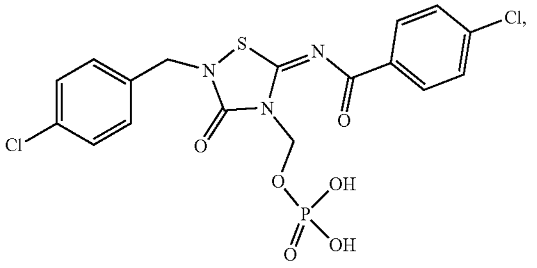

or a pharmaceutically acceptable salt or solvate thereof.

4. The compound according to claim 1, wherein the pharmaceutically acceptable salt is an alkali metal salt, an alkaline earth metal salt or a quaternary ammonium salt of the compound of formula I.

5. The compound according to claim 4, wherein the pharmaceutically acceptable salt is a sodium or potassium salt of the compound of formula I.

6. A pharmaceutical formulation comprising a compound according to claim 1, or a pharmaceutically acceptable salt or solvate thereof, and a pharmaceutically acceptable excipient.

7. The pharmaceutical formulation according to claim 6, wherein the pharmaceutically acceptable excipient is a basic excipient.

8. The pharmaceutical formulation according to claim 6, wherein the pharmaceutically acceptable excipient is selected from the group consisting of magnesium oxide, sodium hydrogen carbonate, potassium hydrogen carbonate, sodium carbonate, potassium carbonate, magnesium carbonate and calcium carbonate, or any combination thereof.

9. The pharmaceutical formulation according to claim 6, further comprising an enteric coating.

10. A process for preparing a compound according to claim 1, wherein the process comprises:

(i) reacting a compound of formula V,

V

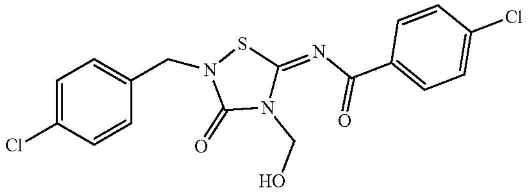

with a suitable acid or acid anhydride; or (ii) reacting a compound of formula VI,

VI

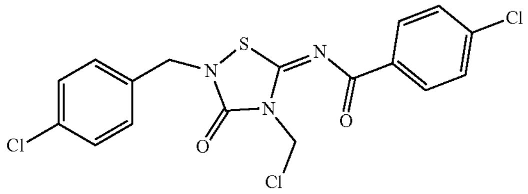

with a suitable acid or suitable acid salt.

11. A method of treating a disorder or condition ameliorated by the activation of AMPK in a subject in need thereof, wherein the disorder or condition is a cardiovascular disease, diabetic kidney disease, diabetes, insulin resistance, non-alcoholic fatty liver disease, non-alcoholic steatohepatitis, pain, opioid addiction, obesity, cancer, inflammation, an autoimmune disease, osteoporosis or an intestinal disease, the method comprising administering a therapeutically effective amount of a compound according to claim 1, or a pharmaceutically acceptable salt thereof, to the subject.

12. The method according to claim 11, wherein the cardiovascular disease is heart failure.

13. The method according to claim 11, wherein the disorder or condition ameliorated by the activation of AMPK is a condition associated with hyperinsulinemia selected from the group consisting of obesity and cardiovascular disease.

14. The method according to claim 11, wherein the compound is administered orally, subcutaneously or intramuscularly.

15. The method according to claim 11, wherein the inflammatory disorder or condition is a chronic inflammatory disease.

16. The method according to claim 11, wherein the disorder or condition is type 2 diabetes.

17. The method according to claim 11, wherein the disorder or condition is obesity.

* * * * *